United States Patent [19]

Beck

[11] Patent Number: 4,618,731
[45] Date of Patent: Oct. 21, 1986

[54] PROCESS FOR PURIFYING 2-PERFLUOROALKYLETHANOLS

[75] Inventor: Leonard H. Beck, Wilmington, Del.

[73] Assignee: E. I. Du Pont de Nemours and Company, Wilmington, Del.

[21] Appl. No.: 800,007

[22] Filed: Nov. 20, 1985

[51] Int. Cl.$^4$ .................. C07C 29/74; C07C 29/88
[52] U.S. Cl. ............................................. 568/842
[58] Field of Search ................................ 568/842

[56] References Cited

U.S. PATENT DOCUMENTS 3,283,012  11/1966  Day .................................... 568/842

Primary Examiner—Howard T. Mars

[57] ABSTRACT

$R_fCH_2CH_2I$ and $R_fI$ present in sufficient quantities so as to cause discoloration of $R_fCH_2CH_2OH$ or products made from it are reacted with an excess of an aqueous alkali metal hydroxide and a $C_1$–$C_3$ alcohol in a closed vessel at a temperature above 80° C. until neither of said iodides can be detected in said final product. NaOH and isopropanol at 100°–115° C. are preferred.

5 Claims, No Drawings

PROCESS FOR PURIFYING 2-PERFLUOROALKYLETHANOLS

FIELD OF THE INVENTION

The present invention relates to a process for purifying alcohols of the formula $R_fCH_2CH_2OH$.

BACKGROUND OF THE INVENTION

The alcohols $R_fCH_2CH_2OH$ are valuable intermediates for preparing oil and water repellants, surface active agents, lubricants and a number of other useful materials. A previously disclosed method for the preparation of those alcohols consists of two reactions carried out in sequence. The first is the reaction of the iodide, $R_fCH_2CH_2I$, with oleum to form the polyfluoroalkyl hydrogen sulfate ester, $R_fCH_2CH_2OSO_2OH$, and $I_2$. The second is the hydrolysis of the ester, $R_fCH_2CH_2OSO_2OH$, with aqueous acid to the alcohol, $R_fCH_2CH_2OH$, and sulfuric acid; see U.S. Pat. No. 3,283,012. While the foregoing method has been used in the industry for some years, it is not without its drawbacks. The 2-perfluoroalkylethanols contain small amounts of $R_fCH_2CH_2I$ and $R_fI$. If those iodides are not removed or converted, discolored products result and corrosive HF is produced. In the past, the 2-perfluoroalkylethanols have been purified by heating them in the presence of small amounts of hydrogen peroxide, thereby oxidizing the iodide to the organic acid, HF and iodine. The resulting waste products are then removed by a sodium bisulfite wash followed by washing with dilute aqueous phosphoric acid.

BRIEF SUMMARY OF THE INVENTION

The present invention relates to an improved process for the purification of 2-perfluoroalkylethanols in which unreacted iodides, having the formulae $R_fCH_2CH_2I$ and $R_fI$, are reacted with an excess of an alkali metal hydroxide and a $C_1$–$C_3$ alcohol in a closed vessel at a temperature above 80° C. until neither of said iodides can be detected in said 2-perfluoroalkylethanols. The organic compounds, $R_fH$ and $R_fCH=CH_2$, resulting from the reaction of $R_fI$ and $R_fCH_2CH_2I$ with the alkali metal hydroxide and the lower alkyl alcohol need not be removed from the 2-perfluoroalkylethanols. An alkali metal iodide is also produced in that reaction, but it is easily removed with the water in the system in which the 2-perfluoroalkylethanols are insoluble. Thus, the process of the present invention effects purification of the 2-perfluoroalkylethanols at considerably lower costs than does the prior art purification procedure described above.

DETAILED DESCRIPTION OF THE INVENTION

The reaction of the iodides can be illustrated as set forth below in which the alcohol is isopropanol:

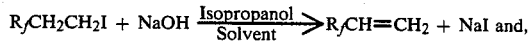

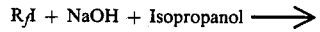

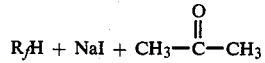

The foregoing reactions are similar to the aluminum isopropoxide reaction known as Meerwein-Ponndorf-Verley Reduction which requires anhydrous conditions. Isopropoxide reductions in aqueous media are unexpected.

The foregoing reactions are usually run at a temperature in the range between about 100° and 115° C., preferably 105°–110° C. While any alkali metal hydroxide is suitable, usually sodium hydroxide or potassium hydroxide is used, preferably the former. Isopropanol is the preferred alcohol as its use results in the formation of acetone. If methanol or ethanol is used, formaldehyde or acetaldehyde is formed, each of which is subject to polymerization under the alkaline conditions used in the process. $R_f$ is a perfluoroalkyl radical containing from 4 to 28 carbons atoms. In the usually commercial operation, $R_fI$ and $R_fCH_2CH_2I$ will each consist of a mixture of such compounds. In such a commercial mixture, less than 5 percent by weight of the perfluoroalkyl radicals will be either 4 or 20 carbons in length, with 80 to 90 percent of the perfluoroalkyl chains containing 6 to 12 carbons, predominantly 6 to 10 carbons, with an average between 6 to 8 carbons.

It is necessary that one use a molar excess of the alkali metal hydroxide in comparison to the amounts of $R_fCH_2CH_2I$ and $R_fI$ being converted. The exact amount of the alkali metal hydroxide that is needed can be determined readily by monitoring the content of those iodides which remain unreacted. Usually, one will use a one-fold molar excess of the alkali metal hydroxide in comparison to the $R_fCH_2CH_2I$ content and approximately ten times that molar excess in connection with $R_fI$. At the same time, one will use an amount of the lower alkyl alcohol which is at least the molar equivalent of the alkali metal hydroxide.

The following example is illustrative of the invention. Unless otherwise indicated, all percentages are by weight and temperatures are in degrees Celsius.

Charge to a 400 ml titanium autoclave: (a) 400 g of a mixture of 2-perfluoroalkylethanols having a molecular weight of about 485 and containing (i) about 3% of a mixture of 2-perfluoroalkylethyl iodides having a molecular weight of about 580 and (ii) about 0.3% of mixture of perfluoroalkyl iodides having a molecular weight of about 550; (b) 15 g of 30% aqueous sodium hydroxide and (c) 8 g of isopropyl alcohol. Seal the autoclave and heat at 110° for two hours. Cool to 70° C. and pour into 200 ml water to extract the isopropyl alcohol, acetone, sodium iodide and excess sodium hydroxide. Stir briefly at 85°–90° C. and separate the bottom purified 2-perfluoroalkylethanol-containing product layer from the above-described aqueous layer. The purified product layer is dried to less than 0.1% water by heating to a pot temperature of 140° C. at atmospheric pressure to remove the remaining isopropyl alcohol and some of the olefin $R_fCH=CH_2$. Thereafter, the purified product is heated at 100° C. and 200 mm Hg for one hour to remove the last traces of water.

I claim:

1. In a process wherein a perfluoroalkylethyl iodide or a mixture of perfluoroalkylethyl iodides is reacted with oleum, the resulting perfluoroalkylethyl hydrogen sulfate or mixture of said sulfates is hydrolyzed in an aqueous sulfuric acid medium, and a perfluoroalkylethanol or a mixture of such ethanols having the formula $R_fCH_2CH_2OH$ is recovered as a final product which contains unreacted iodides having the formulae $R_fCH_2CH_2I$ and $R_fI$ in sufficient quantities so as to cause discoloration of R$_f$CH$_2$CH$_2$OH or products made from it wherein R$_f$ is a perfluoroalkyl radical or a mixture of said radicals containing 4 to 28 carbon atoms, the improvement consisting essentially of reacting said unreacted iodides with an excess of an aqueous alkali metal hydroxide and a C$_1$-C$_3$ alcohol in a closed vessel at a temperature above 80° C. until neither of said iodides can be detected in said final product.

2. The process of claim 1 wherein said temperature is between about 100° and 115° C.

3. The process of claim 2 wherein said temperature is between about 105° and 110° C.

4. The process of claim 1 wherein said alkali metal hydroxide is sodium hydroxide.

5. The process of claim 1 wherein said alcohol is isopropanol.

* * * * *